United States Patent [19]

Durant et al.

[11] E Re. 30,457

[45] Reissued Dec. 23, 1980

[54] PHARMACOLOGICALLY ACTIVE COMPOUNDS

[75] Inventors: Graham J. Durant; Charon R. Ganellin, both of Welwyn Garden City; Robert J. Ife, Stevenage, all of England

[73] Assignee: Smith Kline & French Laboratories Limited, Welwyn Garden City, England

[21] Appl. No.: 933,254

[22] Filed: Aug. 10, 1978

Related U.S. Patent Documents

Reissue of:

[64] Patent No.: 4,084,001
Issued: Apr. 11, 1978
Appl. No.: 744,584
Filed: Nov. 23, 1976

[30] Foreign Application Priority Data

Dec. 1, 1975 [GB] United Kingdom ..... 49248/75

[51] Int. Cl.[2] ..... A61K 31/17
[52] U.S. Cl. ..... 424/322; 260/453.4
[58] Field of Search ..... 424/322; 260/552 R

[56] References Cited

U.S. PATENT DOCUMENTS 3,669,670 6/1972 Haist et al. ..... 96/95

*Primary Examiner*—Stanley J. Friedman
*Attorney, Agent, or Firm*—Joan S. Keps; Richard D. Foggio; William H. Edgerton

[57] ABSTRACT

The compounds are substituted S-(aminoalkyl)-isothioureas which are histamine $H_2$-antagonists. Two specific compounds of the present invention are S-[6-(N′-methylthioureido)hexyl]isothiourea and S-[5-(N′-cyano-N″-methylguanidino)pentyl]isothiourea.

9 Claims, No Drawings

PHARMACOLOGICALLY ACTIVE COMPOUNDS

Matter enclosed in heavy brackets [ ] appears in the original patent but forms no part of this reissue specification; matter printed in italics indicates the additions made by reissue.

This invention relates to pharmacologically active compounds, to methods for preparing these compounds, to pharmaceutical compositions containing these compounds and to methods of blocking histamine $H_2$-receptors by administering these compounds. The compounds of the invention will normally exist as acid addition salts and hydrated salts but, for convenience reference will be made throughout this specification to the parent compounds.

Many physiologically active substances elicit their biological actions by interaction with specific sites known as receptors. Histamine is such a substance and has a number of biological actions. Those biological actions of histamine which are inhibited by drugs commonly called "antihistamines" of which mepyramine, diphenhydramine and chlorpheniramine are typical examples are mediated through histamine $H_1$-receptors (Ash and Schild, Brit. J. Pharmac. Chemother., 27, 427, (1966)). However, other of the biological actions of histamine are not inhibited by "antihistamines" and actions of this type which are inhibited by a compound described by Black et al. (Nature, 236, 385, (1972)) and called burimamide are mediated through receptors which are defined by Black et al. as histamine $H_2$-receptors. Thus histamine $H_2$-receptors may be defined as those histamine receptors which are not blocked by mepyramine but are blocked by burimamide. Compounds which block histamine $H_2$-receptors are referred to as histamine $H_2$-antagonists.

Blockade of histamine $H_2$-receptors is of utility in inhibiting the biological actions of histamine which are not inhibited by "antihistamines". Histamine $H_2$-antagonists are therefore useful, for example, as inhibitors of gastric acid secretion, as anti-inflammatory agents and as agents which act on the cardiovascular system, for example as inhibitors of the effects of histamine on blood pressure. In the treatment of certain conditions, for example inflammation and inhibiting the actions of histamine on blood pressure, a combination of $H_1$- and $H_2$-antagonists is useful.

The compounds of this invention are histamine $H_2$-antagonists. These compounds are represented by the following Formula 1:

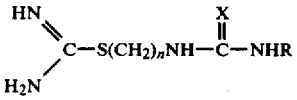

FORMULA 1 wherein n is an integer from 3 to 6; R is lower alkyl or

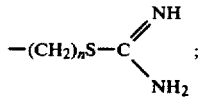

and X is sulphur, NCN or $CHNO_2$, or a pharmaceutically acceptable acid addition salt thereof. It will be understood that the structure illustrated in Formula 1 is only one of several possible representations and that other tautomeric forms are also covered by the present invention. Throughout the present specification by the term "lower alkyl" we mean an alkyl group containing from 1 to 4 carbon atoms.

Preferably X is sulphur or NCN, and particularly preferably NCN.

Particularly useful compounds are those wherein n is 5 or 6. Specific useful compounds falling within the scope of the invention include:

S-[6-(N'-methylthioureido)hexyl]isothiourea

S-[5-(N'-methylthioureido)pentyl]isothiourea

S-[5-(N'-cyano-N''-methylguanidino)pentyl]isothiourea and

S-[6-(N'-cyano-N''-methylguanidino)hexyl]isothiourea

The compounds of Formula 1 may be prepared by treating a compound of Formula 2

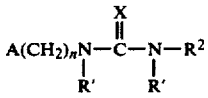

FORMULA 2 wherein n and X are as defined in Formula 1, $R^2$ is lower alkyl or $-(CH_2)_nA$, A is chlorine, bromine, iodine, p-toluenesulphonyloxy, methanesulphonyloxy or other suitable group displaceable by sulphur, R' is hydrogen when X is NCN or $CHNO_2$, and R' is a suitable thiourea protecting group when X is sulphur, with thiourea, and when X is sulphur subsequent removal of the protecting groups R'. Preferably the reaction with thiourea is carried out under essentially anhydrous conditions. Preferably the reaction with thiourea is carried out in the presence of a suitable inert solvent, e.g. acetone, at an elevated temperature e.g. 50° to 150°. Preferred thiourea protecting groups are those where

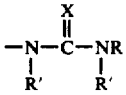

forms a 2-thioxo-4,5-imidazolidinedione or a a 5,5-dialkyl-2-thiobarbiturate ring. These protecting groups may be removed under mildly basic conditions, e.g. treatment with ammonium hydroxide in an aqueous alcohol, and the 5,5-dialkyl-2-thiobarbiturate ring can also be cleaved by refluxing in an aqueous alcohol in the presence of an acid.

The starting materials of Formula 2 wherein X is NCN or $CHNO_2$ and $R^2$ is lower alkyl may be prepared according to the scheme:

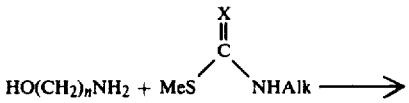

FORMULA 3 FORMULA 4

-continued

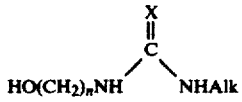

FORMULA 5

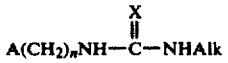

FORMULA 6

In Formulas 4, 5 and 6 Alk represents lower alkyl. A compound of Formula 4, wherein X is NCN or $CHNO_2$, may be reacted with an aminoalkanol of Formula 3 to give a compound of Formula 5, which may be converted into a compound of Formula 6 by standard methods, e.g. treatment with p-toluenesulphonyl chloride in pyridine. An alternative method for preparing the compounds of Formula 4 is to treat dimethyl N-cyanodithioimidocarbonate or 1-nitro-2,2-bis(methylthio)ethylene first with one equivalent of an amine of Formula 3, and then with an excess of a lower alkylamine.

The starting materials of Formula 2 wherein X is NCN or $CHNO_2$ and $R^2$ is $-(CH_2)_nA$ may be prepared by treating dimethyl N-cyanodithioimidocarbonate or 1-nitro-2,2-bis(methylthio)ethylene with at least two equivalents of an amine of Formula 3, to give a compound of Formula 7. Compounds of Formula 7

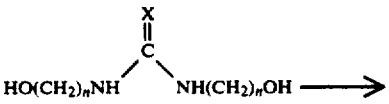

FORMULA 7

X = NCN or $CHNO_2$

-continued

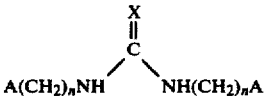

FORMULA 8

X = NCN or $CHNO_2$ may be converted into compounds of Formula 8 e.g. by treatment with p-toluenesulphonyl chloride in pyridine.

The starting materials of Formula 2 wherein X is sulphur and both the groups R' form part of a 2-thioxo-4,5-imidazolidinedione ring may be prepared according to the scheme:

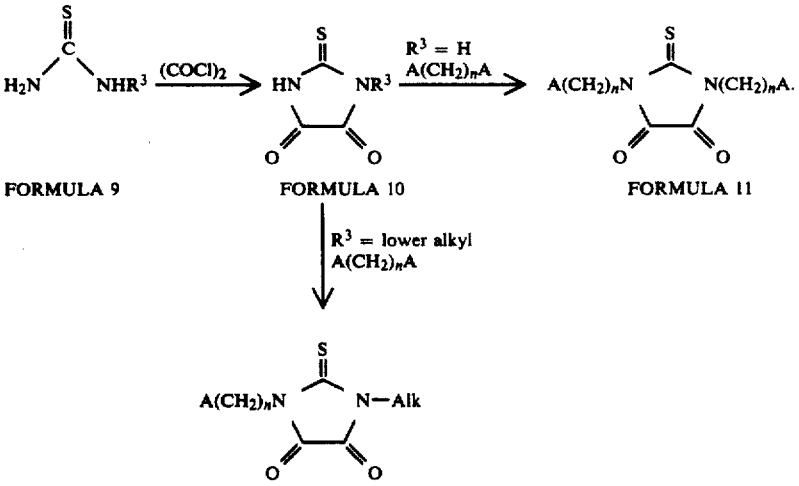

FORMULA 9 FORMULA 10 FORMULA 11

FORMULA 12

A compound of Formula 9 wherein $R^3$ is hydrogen or lower alkyl, is treated with oxalyl chloride to give a compound of Formula 10 which is then treated under anhydrous basic conditions with a compound of formula $A(CH_2)_nA$ where n and A are as defined in Formula 1 to give a compound of Formula 11, or a compound of Formula 12 where Alk is lower alkyl. It will be apparent that at least two molar equivalents of the compound $A(CH_2)_nA$ should be used to prepare a compound of Formula 11 from a compound of Formula 10 wherein $R^3$ is hydrogen.

Compounds of formula 2 wherein both the groups R' form part of a 5,5-dialkyl-2-thiobarbiturate ring may be prepared by treating a compound of Formula 9 with a diethyl 2,2-dialkylmalonate, followed by reactions analogous to those outlined immediately above.

The compounds of Formula 1 block histamine $H_2$-receptors, that is they inhibit the biological actions of histamine which are not inhibited by "antihistamines" such as mepyramine but are inhibited by burimamide. For example, the compounds of this invention have been found to inhibit histamine-stimulated secretion of gastric acid from the lumen-perfused stomachs of rats anaesthetised with urethane, at doses of from 0.5 to 256 micromoles per kilogram intravenously. This procedure is referred to in the above mentioned paper of Ash and Schild. The activity of these compounds as histamine $H_2$-antagonists is also demonstrated by their ability to inhibit other actions of histamine which, according to the above mentioned paper of Ash and Schild, are not mediated by histamine $H_1$-receptors. For example, they inhibit the actions of histamine on the isolated guinea pig atrium and isolated rat uterus.

The compounds of this invention inhibit the basal secretion of gastric acid and also that stimulated by pentagastrin or by food.

In addition, the compounds of this invention show anti-inflammatory activity in conventional tests such as the rat paw oedema or the guinea-pig U.V. erythema tests. In the former the oedema is induced by an irritant, and in the latter the depilated skin of the guinea-pig is exposed to U.V. radiation and an erythema results. Subcutaneous injection of doses of a compound of Formula I reduces the rat paw volume in the former test and reduces the intensity of the guinea-pig erythema in the latter test.

A useful modification of the guinea-pig U.V. erythema test is to irradiate only the whole ear and measure the ear temperature by a thermistor probe. Subcutaneous injection of doses of about 0.1 mmol/kg of a compound of Formula 1 to a guinea-pig reduces the rise in ear temperature caused by U.V. irradiation.

The level of activity of the compounds of this invention is illustrated by the effective dose producing 50% inhibition of gastric acid secretion in the anaesthetised rat and the dose producing 50% inhibition of histamine-induced tachycardia in the isolated guinea-pig atrium.

For therapeutic use, the pharmacologically active compounds of the present invention will normally be administered as a pharmaceutical composition comprising as the or an essential active ingredient at least one such compound in the form of an addition salt with a pharmaceutically acceptable acid and in association with a pharmaceutical carrier therefor. Such addition salts include those with hydrochloric, hydrobromic, hydriodic, sulphuric, acetic and maleic acids and may conveniently be formed by standard procedures, for example by the use of ion-exchange resins to form the required salt.

Pharmaceutical compositions comprising a pharmaceutical carrier and a pharmaceutically acceptable acid addition salt of a compound of Formula 1 and methods of blocking histamine $H_2$-receptors which comprise administering this salt to an animal are also objections of this invention. The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg to about 500 mg. If a liquid carrier is used, the preparation may be in the form of a syrup, emulsion, soft gelatin capsule, sterile injectable liquid contained for example in an ampoule, or an aqueous or nonaqueous liquid suspension.

The pharmaceutical compositions are prepared by conventional techniques involving procedures such as mixing, granulating and compressing or dissolving the ingredients as appropriate to the desired preparation.

The active ingredient will be present in the compositions in an effective amount to block histamine $H_2$-receptors. The route of administration may be oral or parenteral.

Preferably, each dosage unit will contain the active ingredient in an amount of from about 50 mg to about 250 mg.

The active ingredient will preferably be administered one to six times per day. The daily dosage regimen will preferably be from about 150 mg to about 1500 mg.

Advantageously the composition will be made up in a dosage form appropriate to the desired mode of administration, for example as a tablet, capsule, injectable solution or as a cream or ointment for topical application.

The invention is illustrated but in no way limited by the following examples, wherein all temperatures are in degrees Centigrade.

EXAMPLE 1

S-[5-N'-methylthioureido)pentyl]isothiouronium acetate monohydrate (i) Triethylamine (84 ml, 0.60 mole) was added dropwise over a period of 6 hours to a stirred solution of 1-methyl-2-thioxo-4,5-imidazolidinedione (88 g, 0.61 mole) and 1,5-dibromopentane (264 g, 1.20 mole) in dimethylsulphoxide (650 ml) at room temperature. The mixture was allowed to stand overnight and then poured into ice water (3 liters) containing concentrated hydrobromic acid (1 ml). The mixture was extracted with chloroform and the extracts were washed with water, dried over magnesium sulphate and evaporated to give an oil which was treated with hexane to give yellow crystals of 1-(5-bromopentyl)-3-methyl-2-thioxo-4,5-imidazolidinedione (82.3 g), m.p. 48°-50°.

(ii) 1-(5-Bromopentyl)-3-methyl-2-thioxo-4,5-imidazolidinedione (81 g, 0.276 mole) and thiourea (21 g, 0.276 mole) were heated together under reflux in acetone (450 ml) for 21 hours. On cooling in ice yellow crystals of S-[5-(1-(3-methyl-4,5-dioxo-2-thioxoimidazolidinyl))pentyl]isothiourea hydrobromide (77.6 g) were obtained. A sample recrystallised from methanol/ether had m.p. 169°-171°.

(Found: C, 32.6; H, 4.7; N, 15.4; S, 17.5; Br, 21.5% $C_{10}H_{16}N_4O_2.HBr$ requires: C, 32.5; H, 4.6; N, 15.2; S, 17.4; Br, 21.6%)

(iii) S-[5-(1-(3-Methyl-4,5-dioxo-2-thioxoimidazolidyl))pentyl]isothiourea hydrobromide (23 g) was dissolved in methanol (100 ml) and water (10 ml) and to this solution was added ammonium hydroxide (220 ml). The mixture was allowed to stand for 10 min. and a further 50 ml of ammonium hydroxide was added. After a further 5 min. the mixture was cooled in dry ice/acetone and freeze dried at 0.005 mm Hg. The residue was taken up in water, acidified to pH 3 with hydrobromic acid and the insoluble material filtered off. After extraction with ether to remove impurities the aqueous solution was passed through an ion-exchange column (Amberlite IRA 400, acetate form) at 50° and the volume of the eluant reduced to approximately 150 ml. On standing overnight at 5° white crystals were obtained which were recrystallised from water containing a little acetic acid to afford the title compound, m.p. 101°-104°.

(Found: C, 38.5; H, 7.8; N, 18.1; S, 20.5; $C_8H_{18}N_4S_2.CH_3CO_2H.H_2O$ requires: C, 38.4; H, 7.7; N, 17.9; S, 20.5%)

EXAMPLE 2

S-[6-(N'-Methylthioureido)hexyl]isothiouronium acetate monohydrate (i) When, the procedure of Example 1 (i) 1,6-dibromohexane was used in place of 1,5-dibromopentane the product was 1-(6-bromohexyl)-3-methyl-2-thioxo-4,5-imidazolidinedione, m.p. 63°-65° (from hexane).

Found: C, 39.4; H, 4.9; N, 9.2; S, 10.2; Br, 26.2% $C_{10}H_{15}Br\ N_2O_2S$ requires: C, 39.1; H, 4.9; N, 9.1 S, 10.4; Br, 26.0%)

(ii) Reaction of 1-(6-bromohexyl)-3-methyl-2-thioxo-4,5-imidazolidinedione and thiourea by the procedure of Example 1 (ii) and recrystallisation of the product from methanol/ether gave S-[6-(1-(3-methyl-4,5-dioxo-2-thioxoimidazolidinyl))hexyl]-isothiourea hydrobromide, m.p. 131°-133°. (Found: C, 34.8; H, 5.0; N, 14.7; S, 16.5; $C_{11}H_{18}N_4O_2S_2.HBr$ requires: C, 34.5; H, 5.0; N, 14.6; S, 16.7%)

(iii) Alkaline hydrolysis of S-[6-(1-(3-methyl-4,5-dioxo-2-thioxoimidazolidinyl))hexyl]isothiourea using the method described in Example 1 (iii) gave, after recrystallisation from water, S-[6-(N'-methylthioureido)hexyl]isothiouronium acetate monohydrate, m.p. 105°-108°.

Found: C, 40.3; H, 8.0; N, 17.0; S, 19.6; $C_9H_{20}N_4S_2.CH_3CO_2H.H_2O$ requires: C, 40.5; H, 8.0; N, 17.2; S, 19.6%)

EXAMPLE 3

S-[3-(N'-methylthioureido)propyl]isothiouronium acetate

By the procedure of Example 1(i), 1,3-dibromopropane was reacted with 1-methyl-2-thioxo-4,5-imidazolidinedione to yield 1-(3-bromopropyl)-3-methyl-2-thioxo-4,5-imidazolidinedione which, on reaction with thiourea by the procedure of Example 1(ii) gave S-[6-(1-(3-methyl-4,5-dioxo-2-thioxoimidazolidinyl))propyl]isothiourea hydrobromide. Hydrolysis of the latter compound by the procedure of Example 1(iii) and recrystallisation of the product from water gave the title compound, m.p. 141°-143°.

(Found: C, 36.2; H, 6.8; N, 21.2; S, 23.8% $C_6H_{14}N_4S_2.CH_3COOH$ requires: C, 36.1; H, 6.8; N, 21.0; S, 24.1%)

EXAMPLE 4

S-[4-(N'-methylthioureido)butyl]isothiouronium hemisulphate

By the procedure of Example 1(i), 1,4-dibromobutane is reacted with 1-methyl-2-thioxo-4,5-imidazolidinedione to yield 1-(4-bromobutyl)-3-methyl-2-thioxo-4,5-imidazolidinedione which, on reaction with thiourea by the procedure of Example 1(ii) gives S-[4-(1-(3-methyl-4,5-dioxo-2-thioxoimidazolidinyl))butyl]isothiourea hydrobromide, m.p. 113°-114°. Hydrolysis of the latter compound and working up of the product by the general procedure of Example 1(iii) and conversion to the sulphate with ion-exchange resin (Amberlite IRA 400, sulphate form) gave the title product as a hygroscopic amorphous solid, m.p. 63°-65°.

EXAMPLE 5

S-(5-(N'-Cyano-N''-methylguanidino)pentyl)isothiouronium acetate (i) A mixture of 5-aminopentan-1-ol (20 g.) and N-cyano-N',S-dimethylisothiourea (25 g.) in pyridine (130 ml) was heated on a steam-bath for 14 hours, evaporated to dryness, and the residue recrystallised from chloroform/methanol to give N-cyano-N'-(5-hydroxypentyl)-N''-methylguanidine (15.7 g). A recrystallised sample had m.p. 116°-119°.

(Found: C, 51.9; H, 8.8; N, 30.3; $C_8H_{16}N_4O$ requires C, 52.2; H, 8.8; N, 30.4%)

(ii) A solution of p-toluenesulphonyl chloride (9.11 g) in pyridine (40 ml) was added in portions to a stirred solution of N-cyano-N'-(5-hydroxypentyl)-N''-methylguanidine (8.0 g) in pyridine (40 ml) at −10°. The mixture was stirred at 2° for 40 hours and was poured into ice-water. The aqueous mixture was extracted with chloroform, and the extracts were washed with dilute hydrochloric acid and evaporated to give 5-(N'-cyano-N''-methylguanidino)pentyl p-toluenesulphonate (6.3 g) as an orange oil.

(iii) A mixture of 5-(N'-cyano-N''-methylguanidino)-pentyl p-toluenesulphonate (6.3 g), thiourea (1.42 g) in acetone (50 ml) was boiled under reflux for 18 hours. The acetone was decanted off and the residual oil was dissolved in a small volume of water and passed down an ion-exchange column (Amberlite 400, acetate form). Fractions containing the required product were evaporated, and the residue recrystallised from isopropanol to give the title product (2.1 g) m.p. 142°-144°.

EXAMPLE 6

Substitution of 6-aminohexan-1-ol for 5-aminopentan-1-ol in the general procedure of Example 5 leads to the production of S-(6-(N'-cyano-N''-methylguanidino)hexyl)isothiourea.

EXAMPLE 7

Substitution of
(a) 3-aminopropan-1-ol
(b) 4-aminobutan-1-ol
for 5-aminopentan-1-ol in the general procedure of Example 5 leads to the production of
(a) S-(3-(N'-cyano-N''-methylguanidino)propyl)isothiourea
(b) S-(4-(N'-cyano-N''-methylguanidino)butyl)isothiourea

EXAMPLE 8

A mixture of 6-aminohexan-1-ol and 1-methylamino-1-methylthio-2-nitroethylene in ethanol is heated on a steam-bath to give 1-(6-hydroxyhexyl)-1-methylamino-2-nitroethylene. Substitution of 1-(6-hydroxyhexyl)-1-methylamino-2-nitroethylene for N-cyano-N'-(5-hydroxypentyl)-N''-methylguanidine in the procedure of Example 5 (ii and iii) leads to the production of S-[6-((1-methylamino-2-nitrovinyl)amino)hexyl]isothiourea.

EXAMPLE 9

Substitution of
(a) 3-aminopropan-1-ol
(b) 4-aminobutan-1-ol
(c) 5-aminopentan-1-ol
for 6-aminohexan-1-ol in the procedure of Example 8 leads to the production of (a) S-[3-((1-methylamino-2-nitrovinyl)amino)propyl-]isothiourea (b) S-[4-((1-methylamino-2-nitrovinyl)amino)butyl]isothiourea (c) S-[5-((1-methylamino-2-nitrovinyl)amino)pentyl]isothiourea

EXAMPLE 10

N-Butylthiourea is treated with oxalyl chloride to give 1-butyl-2-thioxo-4,5-imidazolidinedione which when substituted for 1-methyl-2-thioxo-4,5-imidazolidinedione in the procedure of Example 1 gives S-[5-(N'-butylthioureido)pentyl]isothiourea.

EXAMPLE 11

Substitution of N-cyano-N'-butyl-S-methylisothiourea for N-cyano-N',S-dimethylisothiourea in the procedure of Example 5 gives S-(5-(N'-cyano-N''-butylguanidino)pentyl)isothiourea

EXAMPLE 12

Substitution of 1-butylamino-1-methylthio-2-nitroethylene for 1-methylamino-1-methylthio-2-nitroethylene in the procedure of Example 8 gives S-[6-((1-butylamino-2-nitrovinyl)amino)hexyl]isothiourea.

EXAMPLE 13

Treatment of 2-thioxo-4,5-imidazolidinedione with an excess of 1,5-dibromopentane and triethylamine gives 1,3-bis(5-bromopentyl)-2-thioxo-4,5-imidazolidinedione, which after treatment with an excess of thiourea and deprotection of the product by the general procedure of Example 1(iii) gives N,N'-bis(5-(S-isothioureido)pentyl)thiourea.

EXAMPLE 14

Heating dimethyl N-cyanodithioimidocarbonate with an excess of 5-aminopentan-1-ol in pyridine gives N-cyano-N',N''-bis(5-hydroxypentyl)guanidine, which may be treated with p-toluenesulphonyl chloride in pyridine and the product heated with thiourea in acetone to give N-cyano-N',N''-bis)5-(S-isothioureido)-pentyl)-guanidine.

EXAMPLE 15

Heating 1-nitro-2,2-bis(methylthio)ethylene with an excess of 5-aminopentan-1-ol in ethanol gives 1,1-bis(5-hydroxypentyl)-2-nitroethylene, which may be treated with p-toluenesulphonyl chloride in pyridine and the product heated with thiourea in acetone to give 1,1-bis(5-(S-isothioureido)pentyl)-2-nitroethylene.

EXAMPLE 16

Passage of aqueous solutions of (a) S-[6-(N'-methylthioureido)hexyl]isothiouronium acetate (b) S-[5-(N'-Cyano-N''-methylguanidino)pentyl]isothiouronium acetate down an ion-exchange column (Amberlite IRA 400, sulphate form) and evaporation and crystallisation of the eluate gives (a) S-[6-(N'-methylthioureido)hexyl]isothiouronium hemisulphate (b) S-[5-(N'-cyano-N''-methylguanidino)pentyl]isothiouronium hemisulphate and use of Amberlite IRA 400, hydrochloride form gives (a) S-[6-(N'-methylthioureido)hexyl]isothiourea hydrochloride S-[5-(N'-cyano-N''-methylguanidino)pentyl]isothiourea hydrochloride.

EXAMPLE 17

Pharmaceutical Composition

| Ingredients | Amounts |
|---|---|
| S-[6-(N'-methylthioureido)hexyl]-isothiouronium hemisulphate | 100 mg |
| Sucrose | 50 mg |
| Starch | 15 mg |
| Talc | 4 mg |
| Stearic Acid | 2 mg |

The ingredients are screened, mixed and filled into a hard gelatin capsule.

EXAMPLE 18

Pharmaceutical Composition

| Ingredients | Amounts |
|---|---|
| S-[6-(N'-methylthioureido)hexyl]-isothiouronium hemisulphate | 125 mg |
| Lactose | 75 mg |

The ingredients are screened, mixed and filled into a hard gelatin capsule.

Similarly, the other compounds of Formula 1 may be formulated into pharmaceutical compositions by the procedures of Examples 17 and 18.

The pharmaceutical compositions prepared as in the foregoing examples are administered to a subject within the dose ranges given hereabove to block histamine $H_2$-receptors and to alleviate inflammation.

What is claimed is:

1. A compound of the formula

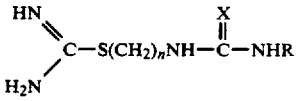

wherein n is an integer from 3 to 6; R is lower alkyl [or]

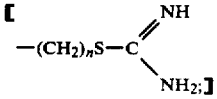

X is sulphur; or a pharmaceutically acceptable acid addition salt thereof.

2. A compound of claim 1 wherein n is 5 or 6.

3. A compound of claim 1, said compound being a salt of S-[6-(N'-methylthioureido)hexyl]isothiourea.

4. A compound of claim 1, said compound being a salt of S-[5-(N'-methylthioureido)pentyl]isothiourea.

5. A compound of claim 1 which is in the form of a pharmaceutically acceptable acid addition salt.

6. A pharmaceutical composition, *in the form of a tablet, capsule or sterile injectable liquid,* to block histamine $H_2$-receptors comprising in an effective amount to block said receptors a compound of [claim 1] *the formula:*

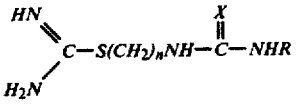

*wherein n is an integer from 3 to 6; R is lower alkyl or*

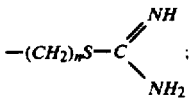

*and X is sulphur* in the form of a pharmaceutically acceptable acid addition salt in combination with a pharmaceutically acceptable diluent or carrier.

7. A pharmaceutical composition of claim 6 in unit dosage form for oral administration.

8. A method of blocking histamine $H_2$-receptors which comprises administering to an animal in need thereof in an effective amount to block said receptors a compound of [claim 1] *the formula:*

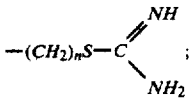

*and X is sulphur; or a pharmaceutically acceptable acid addition salt thereof.*

9. A method of treating inflammation which comprises administering to an animal in need thereof in an effective amount to treat inflammation a compound of [claim 1] *the formula:*

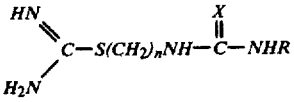

*wherein n is an integer from 3 to 6; R is lower alkyl or*

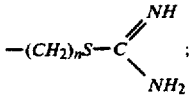

*and X is sulphur; or a pharmaceutically acceptable acid addition salt thereof.*

* * * * *

UNITED STATES PATENT AND TRADEMARK OFFICE

CERTIFICATE OF CORRECTION

PATENT NO. : Re. 30,457

DATED : December 23, 1980

INVENTOR(S) : Graham J. Durant, Charon R. Ganellin and Robert J. Ife

It is certified that error appears in the above—identified patent and that said Letters Patent is hereby corrected as shown below:

Column 10, line 46, after "alkyl" insert -- ; -- .

Column 11, below line 27, insert:

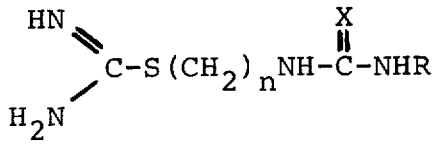

wherein n is an integer from 3 to 6; R is lower alkyl or

Signed and Sealed this

Tenth Day of March 1981

[SEAL]

Attest:

RENE D. TEGTMEYER

Attesting Officer

Acting Commissioner of Patents and Trademarks